United States Patent
Hattori et al.

(10) Patent No.: US 12,400,540 B2
(45) Date of Patent: Aug. 26, 2025

(54) FIRST AID PRESENTATION SYSTEM, FIRST AID PRESENTATION METHOD, AND PROGRAM

(71) Applicant: MITSUBISHI HEAVY INDUSTRIES, LTD., Tokyo (JP)

(72) Inventors: Miri Hattori, Yokohama (JP); Hiroyasu Ishigaki, Yokohama (JP); Daisuke Goto, Yokohama (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 18/037,507

(22) PCT Filed: Nov. 25, 2021

(86) PCT No.: PCT/JP2021/043213
§ 371 (c)(1),
(2) Date: May 17, 2023

(87) PCT Pub. No.: WO2022/163102
PCT Pub. Date: Aug. 4, 2022

(65) Prior Publication Data
US 2024/0021071 A1 Jan. 18, 2024

(30) Foreign Application Priority Data
Jan. 29, 2021 (JP) .................. 2021-013814

(51) Int. Cl.
*G08B 29/20* (2006.01)
*G16H 30/40* (2018.01)
(52) U.S. Cl.
CPC ............ *G08B 29/20* (2013.01); *G16H 30/40* (2018.01)

(58) Field of Classification Search
CPC ... A63F 13/30; G05B 19/4083; G05B 23/027; G05B 23/0272; G05B 2219/24086;
(Continued)

(56) References Cited

U.S. PATENT DOCUMENTS 6,450,818 B1 9/2002 Ogawa et al.
9,348,332 B2 * 5/2016 Morita ................ G06F 11/2257
(Continued)

FOREIGN PATENT DOCUMENTS

CN 110874913 A 3/2020
CN 110994788 A * 4/2020 ............. H02B 15/02
(Continued)

OTHER PUBLICATIONS

International Search Report dated Jan. 25, 2022, issued in counterpart Application No. PCT/JP2021/043213, with English Translation. (6 pages).
(Continued)

*Primary Examiner* — Stephen R Burgdorf
(74) *Attorney, Agent, or Firm* — WHDA, LLP

(57) ABSTRACT

The first aid presentation system comprises: a storage unit that stores one or more pieces of notification information associated with one another from among notification information received from one or more monitoring targets, and one or more pieces of registration information registered by a user and information representing a first aid for the monitoring target that correspond to the notification information; a presentation unit that acquires, from the storage unit, one or more pieces of registration information and a first aid that correspond to notification information associated with specified notification information and that presents the one or more pieces of registration information and the
(Continued)

first aid; and a registration unit that newly registers registration information in association with the specified notification information.

8 Claims, 13 Drawing Sheets

(58) Field of Classification Search
CPC .......... G05B 2219/24091; G06F 11/00; G06F 16/29; G06F 21/32; G06Q 10/02; G06Q 10/06; G06Q 10/06313; G06Q 30/00; G06Q 30/02; G06Q 30/0201; G08B 29/20; G16H 30/40; H04M 7/0012
USPC ........................................................ 340/506
See application file for complete search history.

(56) References Cited

U.S. PATENT DOCUMENTS

| 10,698,398 | B2 | 6/2020 | Kishi et al. |
| 2010/0228364 | A1 | 9/2010 | Ohashi et al. |
| 2010/0228725 | A1 | 9/2010 | Ohashi et al. |
| 2011/0276985 | A1* | 11/2011 | Takatsu ............... H04L 69/329 719/318 |
| 2014/0267566 | A1* | 9/2014 | Hamada .............. H04L 65/4038 348/14.08 |
| 2016/0027288 | A1 | 1/2016 | Toda |
| 2016/0078750 | A1* | 3/2016 | King ..................... A61B 5/002 340/506 |
| 2016/0085235 | A1 | 3/2016 | Kamijo |
| 2016/0328954 | A1 | 11/2016 | Ramadoss et al. |
| 2018/0017959 | A1 | 1/2018 | Pandian et al. |
| 2019/0014004 | A1* | 1/2019 | Horiuchi ............. H04L 41/0893 |
| 2020/0061768 | A1 | 2/2020 | Morita et al. |
| 2020/0096984 | A1 | 3/2020 | Kishi et al. |
| 2020/0169483 | A1* | 5/2020 | Kursun .............. G06Q 20/3678 |
| 2020/0327029 | A1 | 10/2020 | Prakash et al. |
| 2023/0386629 | A1* | 11/2023 | Pfister ................... G16H 15/00 |

FOREIGN PATENT DOCUMENTS

| JP | 2000-194414 A | 7/2000 |
| JP | 2001-022441 A | 1/2001 |
| JP | 2010-182142 A | 8/2010 |
| JP | 2010-204887 A | 9/2010 |
| JP | 2010-211377 A | 9/2010 |
| JP | 2011-154456 A | 8/2011 |
| JP | 2012-059151 A | 3/2012 |
| JP | 2014-203116 A | 10/2014 |
| JP | 2016-031604 A | 3/2016 |
| JP | 2016-066200 A | 4/2016 |
| JP | 2016-212875 A | 12/2016 |
| JP | 2017-097628 A | 6/2017 |
| JP | 2018-097494 A | 6/2018 |
| JP | 2018-120456 A | 8/2018 |
| JP | 2020-038464 A | 3/2020 |
| JP | 2020-173683 A | 10/2020 |
| TW | 201631426 A | 9/2016 |
| WO | 2018/139586 A1 | 8/2018 |

OTHER PUBLICATIONS

Written Opinion dated Jan. 25, 2022, issued in counterpart Application No. PCT/JP2021/043213, with English Translation. (8 pages).

* cited by examiner

FIG. 5

ALARM/EVENT FEED

| OCCURRENCE DATE AND TIME | ALARM NAME | STATE | UNIT | DEVICE NAME |
|---|---|---|---|---|
| 11-01-2020 01:52:21 | ABNORMALITY A | ON | UNIT A | DEVICE A |
| 11-01-2020 01:50:34 | ABNORMALITY B | OFF | UNIT B | DEVICE B |
| | | | | |
| | | | | |
| | | | | |
| | | | | |

FIRST AID PRESENTATION SYSTEM, FIRST AID PRESENTATION METHOD, AND PROGRAM

TECHNICAL FIELD

The present disclosure relates to a first aid presentation system, a first aid presentation method, and a program. The present application claims priority based on Japanese Patent Application No. 2021-013814 filed in Japan on Jan. 29, 2021, the contents of which are incorporated herein by reference.

BACKGROUND ART

PTL 1 discloses the following remote monitoring control system. That is, a remote monitoring control system described in PTL 1 is a remote monitoring control system including: a terminal that is connected to a plurality of remote monitoring control devices via a transmission path and that is connected to any remote monitoring control device, in which the terminal includes a failure recovery database that records known failure contents in the past; a recovery history database that records a history of recovery handling; an input unit that inputs the failure content; a dialog guiding unit that provides a recovery procedure related to a failure content in a dialog guiding manner; and an output unit in which a malfunction state is notified and a failure status is displayed.

CITATION LIST

Patent Literature

[PTL 1] Japanese Unexamined Patent Application Publication No. 2014-203116

SUMMARY OF INVENTION

Technical Problem

In the remote monitoring control system disclosed in PTL 1, the recovery procedure that is related to a failure content is provided in a dialog guiding manner. Therefore, there is a problem that an inappropriate recovery procedure may be presented when there is an error in a response at the time of guiding a dialogue or it may take an inappropriate amount of time at the time of guiding a dialogue.

The present disclosure has been made to solve the above problems, and an object of the present disclosure is to provide a first aid presentation system, a first aid presentation method, and a program capable of appropriately presenting a first aid.

Solution to Problem

In order to solve the above-described problem, a first aid presentation system according to the present disclosure includes: a storage unit that stores one or a plurality of pieces of notification information associated with notification information received from one or a plurality of monitoring targets, information representing a first aid for the monitoring target with respect to the notification information, and one or a plurality of pieces of registration information registered by a user; a presentation unit that acquires, from the storage unit, the first aid with respect to notification information associated with designated notification information and the one or the plurality of pieces of registration information, and that presents the first aid and the one or the plurality of pieces of registration information; and a registration unit that newly registers the registration information with respect to the designated notification information.

A first aid presentation method according to the present disclosure includes: by using a storage unit that stores one or a plurality of pieces of notification information associated with notification information received from one or a plurality of monitoring targets, information representing a first aid for the monitoring target with respect to the notification information, and one or a plurality of pieces of registration information registered by a user, a presentation step of acquiring, from the storage unit, the first aid with respect to notification information associated with designated notification information and the one or the plurality of pieces of registration information, and presenting the first aid and the one or the plurality of pieces of registration information; and a registration step of newly registering the registration information with respect to the designated notification information.

A program according to the present disclosure for causing a computer to execute: by using a storage unit that stores one or a plurality of pieces of notification information associated with notification information received from one or a plurality of monitoring targets, information representing a first aid for the monitoring target with respect to the notification information, and one or a plurality of pieces of registration information registered by a user, a presentation step of acquiring, from the storage unit, the first aid with respect to notification information associated with designated notification information and the one or the plurality of pieces of registration information, and presenting the first aid and the one or the plurality of pieces of registration information; and a registration step of newly registering the registration information with respect to the designated notification information.

Advantageous Effects of Invention

According to a first aid presentation system, a first aid presentation method, and a program of the present disclosure, a first aid can be appropriately presented.

BRIEF DESCRIPTION OF DRAWINGS

FIG. 5 is a schematic diagram illustrating an example of display in a user terminal illustrated in FIG. 1.

DESCRIPTION OF EMBODIMENTS

Figure 1:
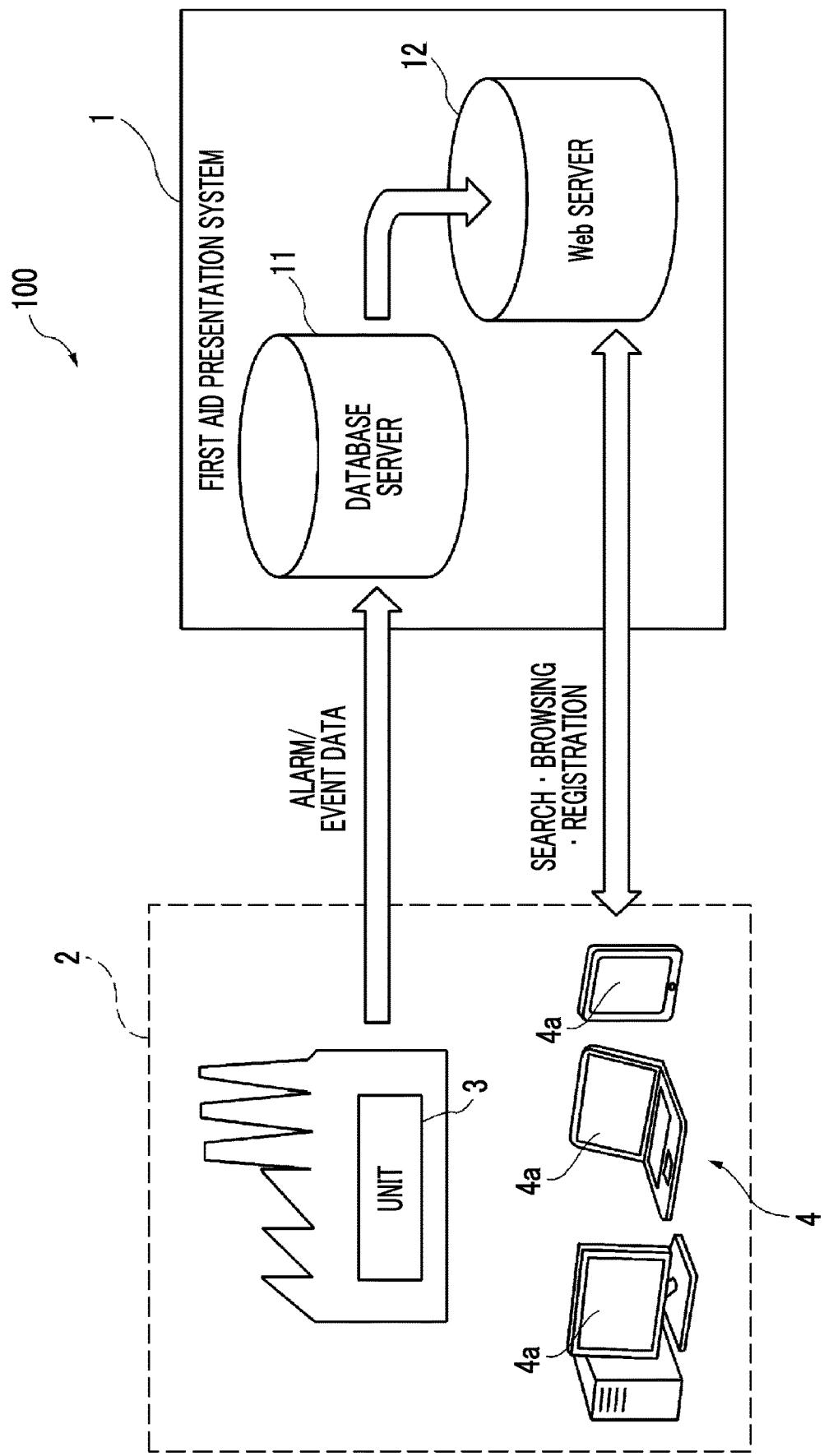
FIG. 1 is a system diagram illustrating an example of a configuration of a first aid presentation system according to an embodiment of the present disclosure.

Hereinafter, a first aid presentation system, a first aid presentation method, and a program according to an embodiment of the present disclosure will be described with reference to the drawings. It should be noted that the same reference numerals are used for the same or corresponding configurations in the respective drawings, and the description thereof will be omitted as appropriate.

First Embodiment

Figure 2:
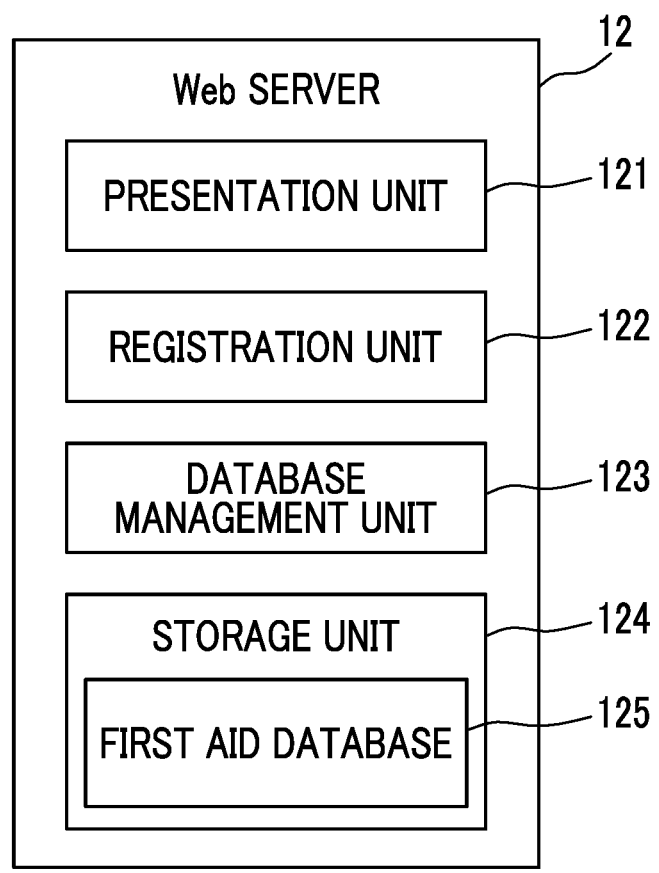
FIG. 2 is a block diagram illustrating an example of a configuration of a web server illustrated in FIG. 1.
Figure 3:
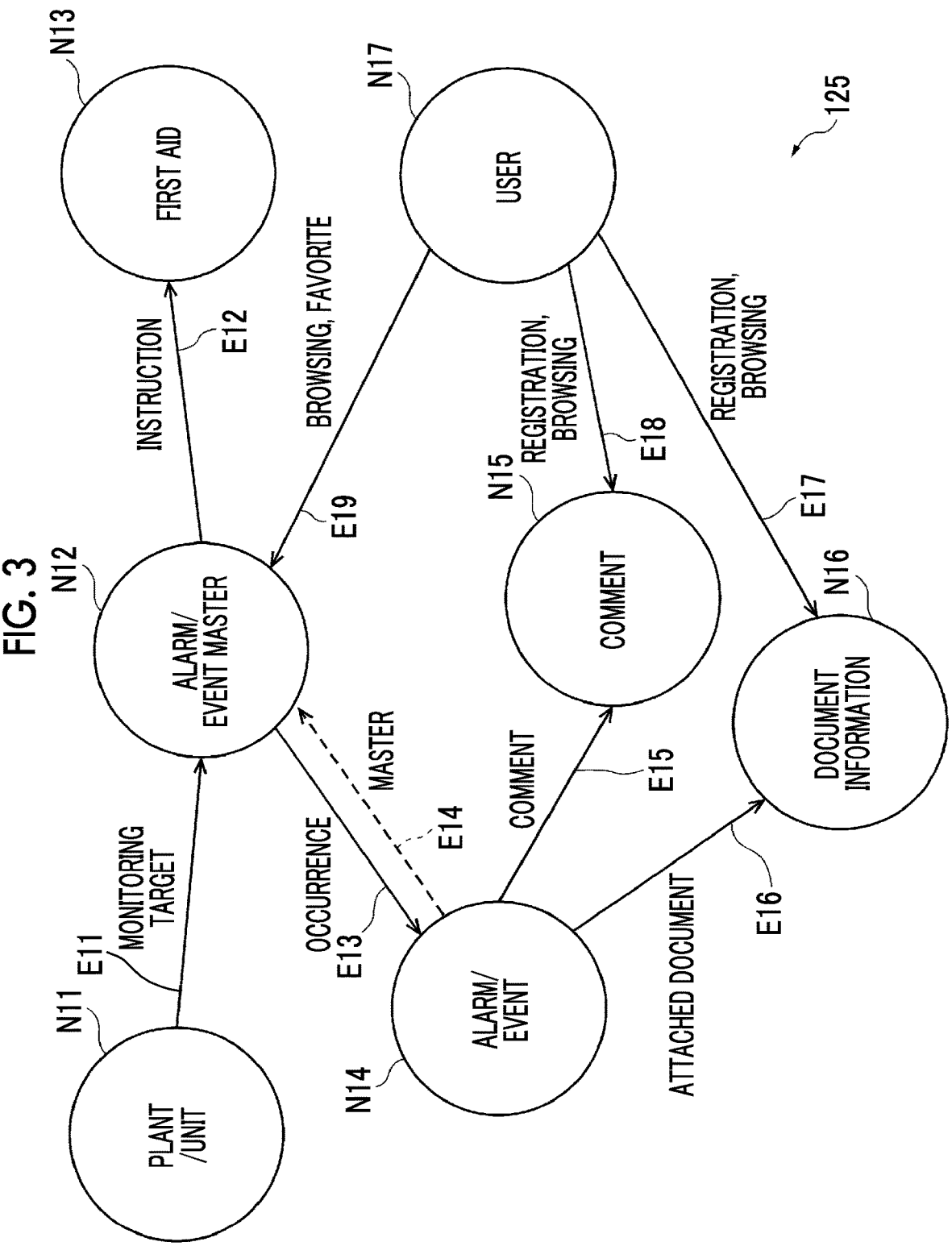
FIG. 3 is a schematic diagram illustrating an example of a configuration of a first aid database illustrated in FIG. 2.
Figure 4:
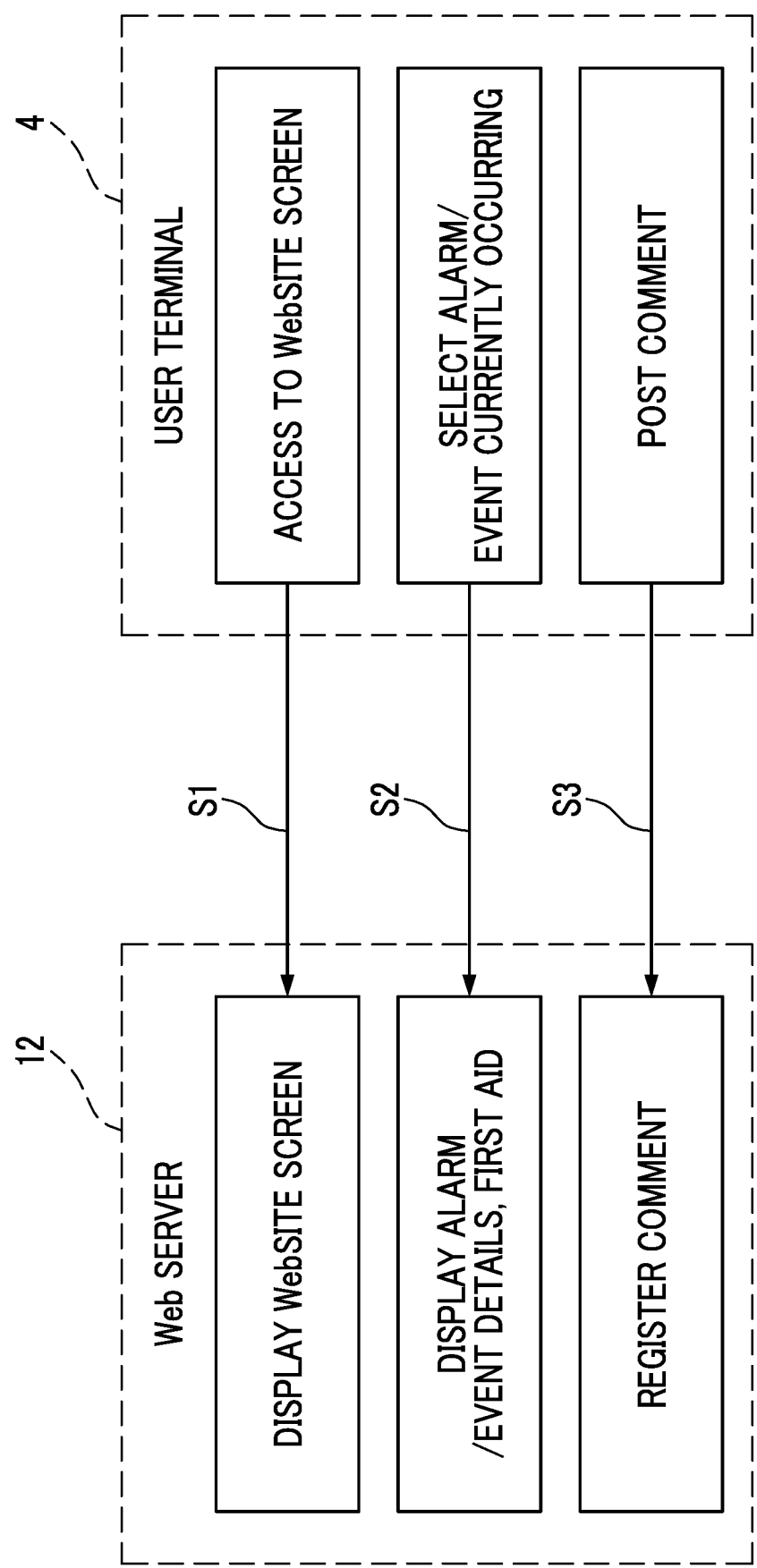
FIG. 4 is a flowchart illustrating an outline of an example of an operation of the first aid presentation system according to the embodiment of the present disclosure.
Figure 6:
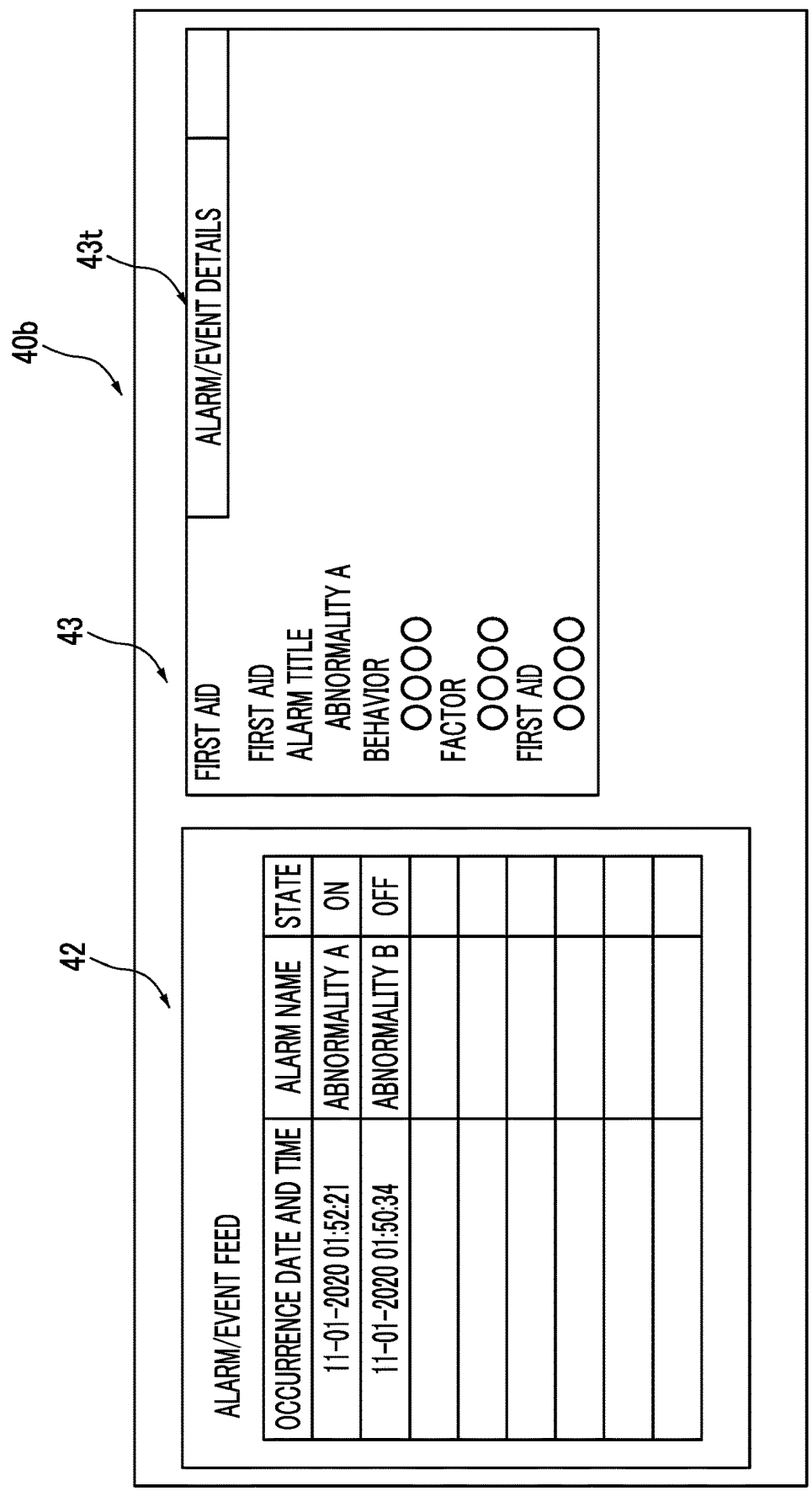
FIG. 6 is a schematic diagram illustrating an example of display in the user terminal illustrated in FIG. 1.
Figure 7:
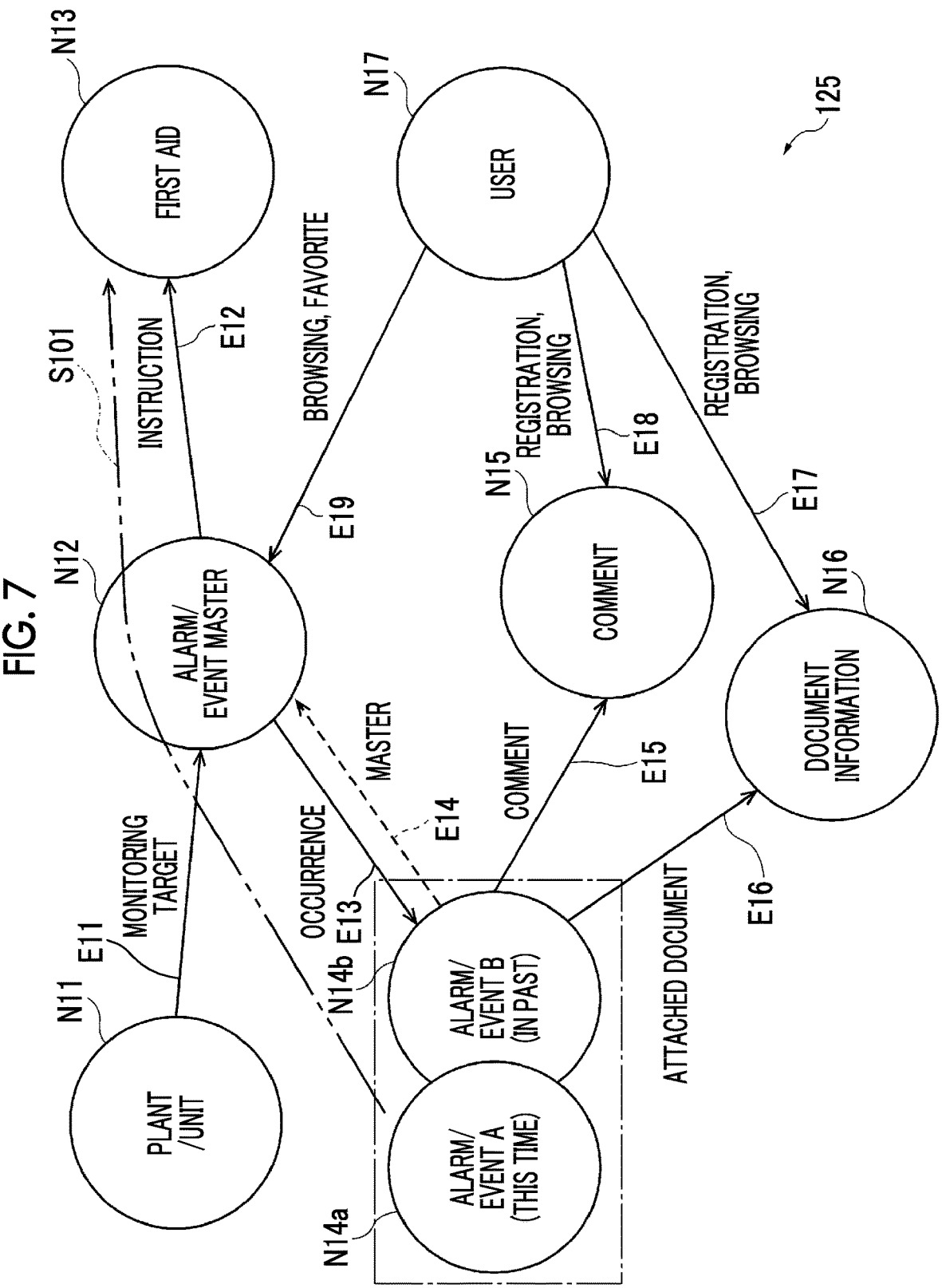
FIG. 7 is a schematic diagram illustrating an example of search in the first aid database illustrated in FIG. 2.
Figure 8:
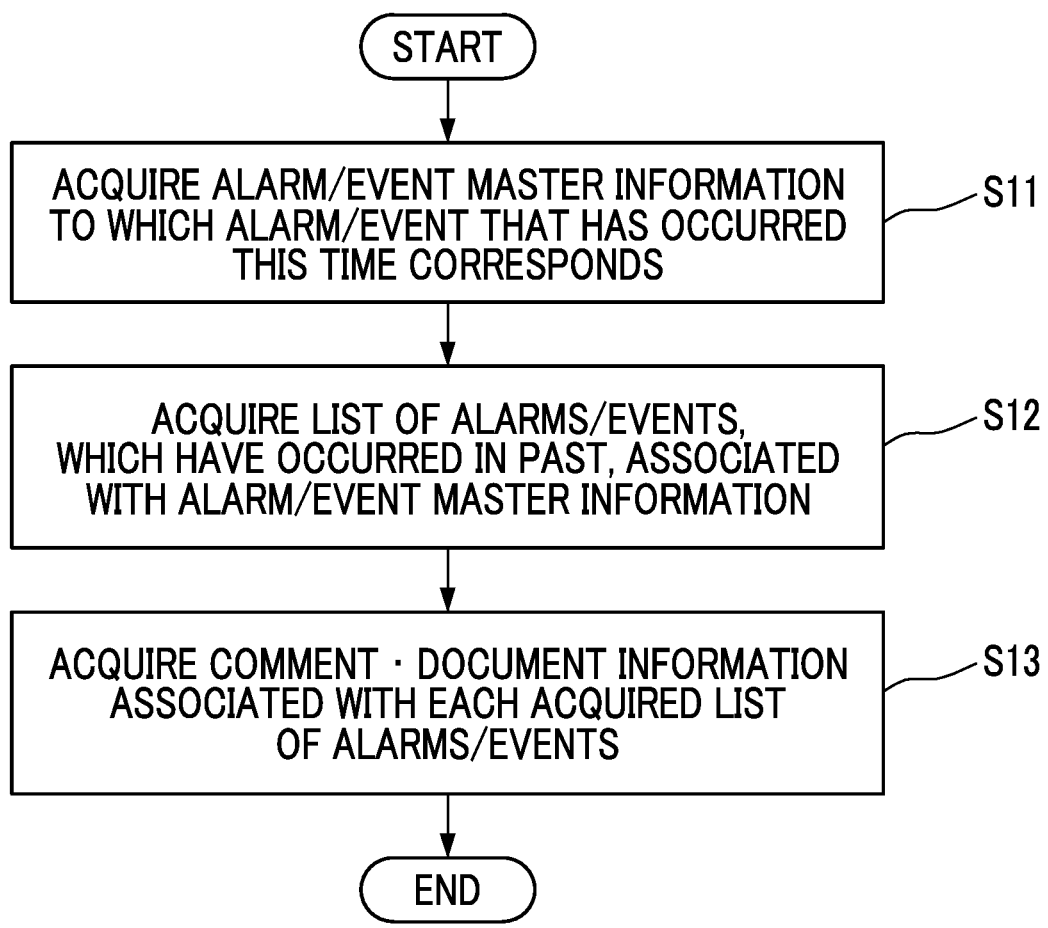
FIG. 8 is a flowchart illustrating an example of an operation of the first aid presentation system according to the embodiment of the present disclosure.
Figure 9:
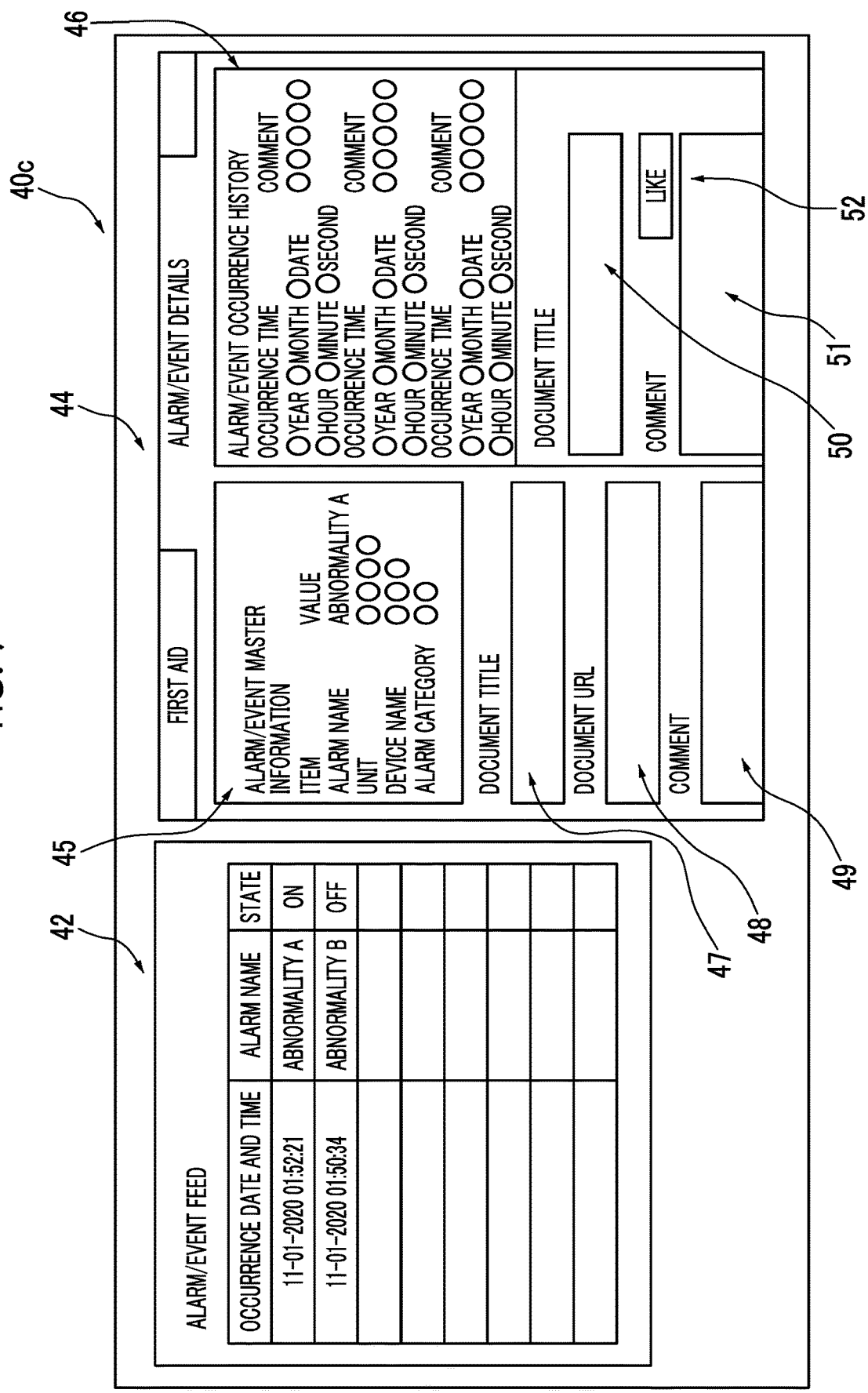
FIG. 9 is a schematic diagram illustrating an example of display in the user terminal illustrated in FIG. 1.
Figure 10:
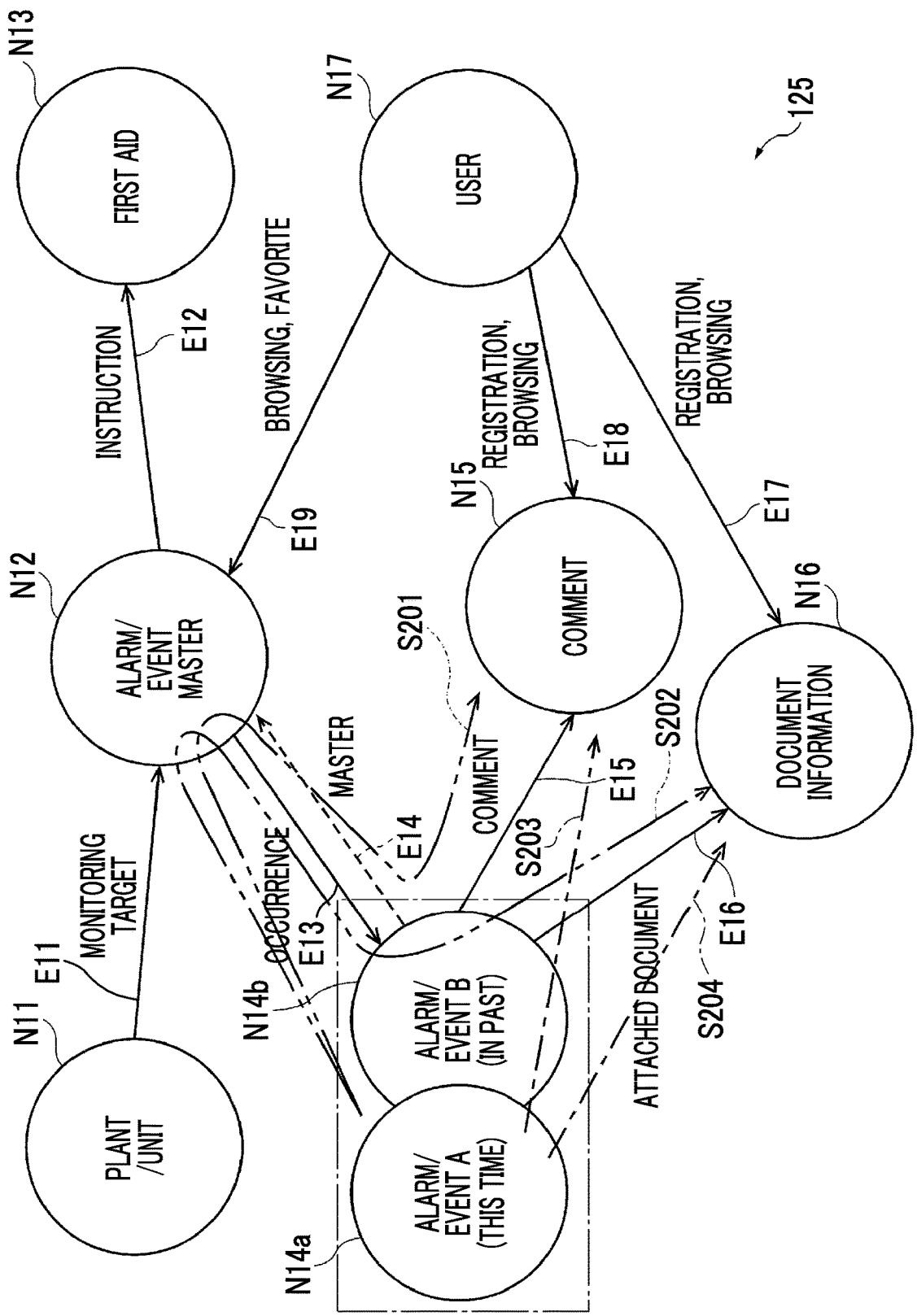
FIG. 10 is a schematic diagram for describing an example of an operation of the first aid presentation system according to the embodiment of the present disclosure.
Figure 11:
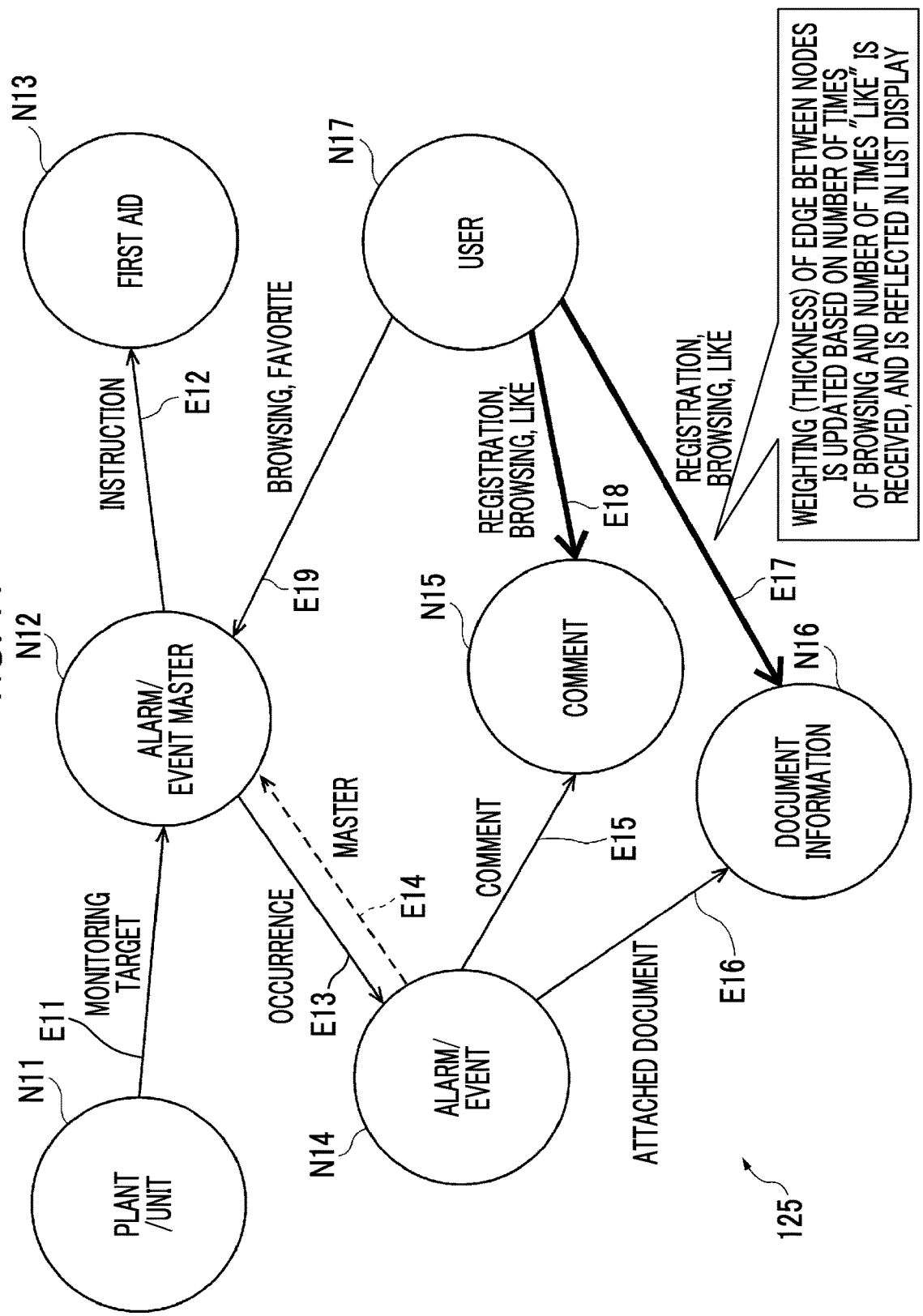
FIG. 11 is a schematic diagram for describing an example of an operation of the first aid presentation system according to the embodiment of the present disclosure.

FIG. 1 is a system diagram of a first aid presentation system according to a first embodiment of the present disclosure. FIG. 2 is a block diagram illustrating an example of a configuration of a web server 12 illustrated in FIG. 1. FIG. 3 is a schematic diagram illustrating an example of a configuration of the first aid database 125 illustrated in FIG. 2. FIG. 4 is a flowchart illustrating an outline of an example of an operation of the first aid presentation system 1 according to a first embodiment. FIG. 5 and FIG. 6 are schematic diagrams illustrating an example of display in a user terminal 4 illustrated in FIG. 1. FIG. 7 is a schematic diagram illustrating an example of search in the first aid database 125 illustrated in FIG. 2. FIG. 8 is a flowchart illustrating an example of an operation of the first aid presentation system 1 according to the embodiment of the present disclosure. FIG. 9 is a schematic diagram illustrating an example of display in the user terminal 4 illustrated in FIG. 1. FIG. 10 and FIG. 11 are schematic diagrams for describing an example of an operation of the first aid presentation system 1 according to the embodiment of the present disclosure.

Example of Configuration of First Aid Presentation System

The first aid presentation system 1 illustrated in FIG. 1 includes a database server 11 and a web server 12 as a functional configuration composed of a combination of a computer, hardware such as a peripheral device of the computer, and software such as a program executed by the computer and data processed by the computer. In this case, the first aid presentation system 1 is configured as one element of a remote monitoring system 100 that remotely monitors alarm/event data generated from a monitoring target such as a unit 3 provided in a plant 2 such as a power plant. The first aid presentation system 1 is a system that searches for and presents a first aid with respect to an alarm/event generated from the plant 2.

The database server 11 receives the alarm/event data transmitted from the plant 2, accumulates the received alarm/event data in a database, and manages the received alarm/event data. The alarm/event data is information generated by a computer (not illustrated) that monitors the monitoring target and represents, for example, date and time when an abnormality is recognized, identification information of the monitoring target, a content of the abnormality, and the like, when a predetermined abnormality (an event indicating an abnormal state) is recognized, or when a predetermined state or a predetermined status change (an event indicating a normal state, an abnormal state, or the like) is recognized, using the unit 3, an apparatus, a device, facility, or the entire plant as the monitoring target. The alarm/event data is notification information that includes alarm data, which is information related to an alarm generated from the monitoring target, and event data, which is information related to an event generated from the monitoring target, (or at least one of those), and that is notified from the monitoring target to the first aid presentation system 1 or the like.

The web server 12 provides functions such as search, browsing, and registration to the user terminal 4 on a web system through a network and provides information indicating a first aid. The user terminal 4 is, for example, a terminal such as a server, a desktop personal computer, a notebook personal computer, or a tablet terminal, and includes a display unit 4a. For example, as illustrated in FIG. 2, the web server 12 includes a presentation unit 121, a registration unit 122, a database management unit 123, and a storage unit 124 as a functional configuration composed of a combination of hardware and software. Further, the storage unit 124 stores the first aid database 125. Here, an example of a configuration of the first aid database 125 will be described with reference to FIG. 3.

The first aid database 125 illustrated in FIG. 3 is configured as a graph database. The graph database is a database having a graph structure and represents a "relationship" between nodes by using three elements of a "node", an "edge", and a "property". The node represents a target object, the edge represents a relationship between the nodes, and the property represents attributes of the node and the edge. The graph database has a high-speed search that traces the connection, is less susceptible to growth in data amount as compared to a relational database, or the like, which search the entire database, and has a high-speed search that traces the connection. Further, the data definition is easy to visually understand from the developer's point of view. The first aid database 125 illustrated in FIG. 3 has nodes N11 to N17 and edges E11 to E19. Further, in FIG. 3, only one of each type of node, which is classified by a label, is shown for each type. However, the number of nodes is not limited to one, and is normally plural.

The node N11 is a node that represents the monitoring target such as the plant or the unit. The node N11 is associated with (or related to) the node N12 through the edge E11.

The node N12 is a node that represents master information of alarm/event (alarm/event master information). It is the basic data of alarm data or the event data. For example, the node N12 has properties such as an alarm name, a unit name, a device name, and an alarm category. The node N12 is associated with the node N13 by using the edge E12 of instruction and is associated with the node N14 by using the edge E13 of occurrence.

The node N13 is a node representing a first aid (the first aid) and represents the first aid or the like for the alarm/event represented by the node N12. The node N13 has, for example, properties such as an alarm name (an alarm title), a behavior, a factor, and a first aid.

The node N14 is a node representing an alarm or an event that has occurred in the plant 2. The node N14 has properties such as an occurrence date and time, an alarm name (an event name), a state, a unit, and a device name. The node N14 is associated with the node N15 by using the edge E15 of comment and is associated with the node N16 by using the edge E16 of attached document. Note that, the node N14 does not extend the edge E14 of master, which is toward the node N12 indicated with the dashed line, and the connection to the node N12 is defined by tracing back the edge E13 of occurrence. According to this, the amount of information can be saved, but when the frequency of tracing is high, the edge may be defined.

The node N15 is a node representing a comment (the registration information) registered by the user with respect to the alarm/event of the node N14. The comment is, for example, a sentence related to the first aid for the alarm/event. The node N15 has properties such as character information representing a content of the comment. The node N16 is a node representing document information (the registration information) registered by the user with respect to the alarm/event of the node N14. The document information is, for example, a document (a document, a document file that can be downloaded on a website, a web page, or the like) referred to at the time of the first aid for the alarm/event. The node N16 has properties such as a document name and a uniform resource locator (URL) of a reference destination of the document.

Further, in the present embodiment, the registration information is information representing at least one of a comment, which is related to the first aid for the alarm/event designated by the user, or a document, which is referred at the time of the first aid for the designated alarm/event. The registration information is, for example, information that includes at least one of the comment and the document information registered by the user. Further, the registration information is information that represents at least one of a comment, which is related to the first aid for the monitoring target related to the designated notification information by the user, or a document, which is referenced at the time of the first aid for the monitoring target related to the designated notification information.

The node N17 is a node representing a user. The node N17 has, for example, properties such as years of experience of the user and a department to which the user belongs. When the comment or the document information is registered or browsed, or when "Like" (or "Favorite") that represents helpful feedback with respect to the comment or the document is registered, the node N17 is used to record a behavior history thereof. The node N17 is associated with the node N16 by using the edge E17 of registration/browsing, is associated with the node N15 by using the edge E18 of registration/browsing, and is associated with the node N12 by using the edge E19 of browsing/"Favorite".

In the present embodiment, the first aid database 125 has the following associations. That is, each node of alarm/event (data) (for example, node N14) is associated with each node of alarm/event master (for example, the node N12). Further, the node of alarm/event master (for example, the node N12) is associated with the node of first aid (for example, the node N13). Further, the node of alarm/event master (for example, the node N12) is associated with one or a plurality of nodes of alarm/event (for example, the node N14 and a plurality of nodes of alarm/event other than the node N14 (not illustrated)). Further, the node of alarm/event (for example, the node N14) is associated with the node of comment (for example, the node N15) and the node of document information (the node N16). In this case, the node of alarm/event (for example, the node N14) is associated with another node of alarm/event and is associated with the node of the comment or the node of document information, which is associated with the other node of alarm/event, via the node of alarm/event master (for example, the node N12). Summarizing these associations together, the first aid database 125 stores one or a plurality of pieces of notification information associated with notification information received from one or a plurality of monitoring targets, information representing a first aid for the monitoring target with respect to the notification information, and one or a plurality of pieces of registration information registered by the user.

Returning to FIG. 2, the presentation unit 121 refers to the first aid database 125, acquires, from the storage unit 124, the first aid associated with the alarm/event master information corresponding to the alarm/event designated by the user and one or a plurality of comments or a plurality of pieces of document information (the registration information) recorded in association with one or a plurality of same or similar alarms/events associated with the relevant alarm/event master information, and presents the first aid and the one or the plurality of comments or the plurality of pieces of document information to the user terminal 4. That is, the presentation unit 121 acquires, from the storage unit 124, the first aid with respect to the notification information associated with the designated notification information and one or a plurality of pieces of registration information, and presents the first aid and the registration information.

Further, the registration unit 122 newly registers the comment or the document information (the registration information) in the first aid database 125 in association with the alarm/event designated by the user. That is, the registration unit 122 newly registers the registration information with respect to the designated notification information.

Further, the database management unit 123 searches for and updates the first aid database 125 in accordance with instructions from the presentation unit 121, the registration unit 122, and the like.

Example of Operation of First Aid Presentation System

Next, an example of an operation of the first aid presentation system 1 illustrated in FIG. 1 and FIG. 2 will be described with reference to FIG. 4 to FIG. 11. FIG. 4 illustrates a flow of processing of accessing a website screen displayed by the web server 12 from the user terminal 4 by the user (step S1), for example, selecting an alarm/event that is currently occurring and checking detailed information and a first aid for that alarm/event (step S2), and further registering a comment for the alarm/event (step S3).

In step S1, the web server 12 (the presentation unit 121) presents information for displaying a screen 40a illustrated in FIG. 5, for example, on the user terminal 4. The screen 40a illustrated in FIG. 5 includes a list 41 of alarm/event data (two in this example) displayed by the user by designating, for example, the plant 2, the unit 3, or the like. In this case, in the list 41, each record representing the alarm/event data includes each item of the occurrence date and time, the alarm name, the state (whether or not the state is continued), the unit, and the device name.

In step S2, assuming that the user selects, for example, the top alarm/event data ("abnormality A") on the screen 40a, the web server 12 (the presentation unit 121) presents information for displaying a screen 40b illustrated in FIG. 6 on the user terminal 4, for example. The screen 40b illustrated in FIG. 6 includes a list 42 of alarm/event data and a display region 43 representing the first aid (the first aid) information corresponding to the selected alarm/event data. Here, processing of searching for the first aid corresponding to the designated alarm/event data from the first aid database 125 will be described with reference to FIG. 7. The first aid database 125 illustrated in FIG. 7 is different from the first aid database 125 described with reference to FIG. 3 in that the node N14 is changed to two nodes of the node N14a and the node N14b. The node N14b is a node that corresponds to the node N14 illustrated in FIG. 3 that is registered in the past (however, assuming the node representing an alarm/event B), and the node N14a is a node that represents an alarm/event A that has newly occurred this time. Note that, the node N14a and the node N14b are alarm/event data of the same type or the same category, and an edge (not illustrated) is extended from the node N12 to the node N14a. In the example illustrated in FIG. 7, as indicated by an arrow S101, by tracing from node N14a to node N12 and from node N12 to node N13, the first aid with respect to the alarm/event data of node N14a can be searched.

Next, in step S2, assuming that a tag 43t, which displays the alarm/event detailed information, is clicked on the screen 40b illustrated in FIG. 6, in the flow of processing illustrated in FIG. 8, the web server 12 (the presentation unit 121) presents information for displaying, for example, a screen 40c illustrated in FIG. 9 in the user terminal 4. First, the web server 12 (the presentation unit 121) acquires the alarm/event master information to which the alarm/event that has occurred this time corresponds (step S11). Next, the web server 12 (the presentation unit 121) acquires a list of the alarms/events, which have occurred in the past, associated with the alarm/event master information (step S12). Next, the web server 12 (the presentation unit 121) acquires the comment/document information associated with each acquired list of alarms/events (step S13). In this case, by tracing each node as indicated by an arrow S201 and an arrow S202 in FIG. 10, the list of alarms/events, which have occurred in the past, associated with the alarm/event master information can be acquired. Note that, the screen 40c illustrated in FIG. 9 includes a display region 45 for the alarm/event master information and a display region 46 for an alarm/event occurrence history (the list of alarms/events) associated with the same node N12 of alarm/event master in the display region 44 related to the alarm/event details. Further, the display region 46 includes occurrence time of each alarm/event included in the list and the content (a part) of the comment registered in association with each alarm/event. Further, the display region 44 includes an input region 47 of a document title, an input region 48 of a document URL, and an input region 49 of a comment to be registered with respect to the alarm/event that has occurred this time. Furthermore, the display region 46 includes a ring button 50 (a download button) for the document registered in association with the past alarm/event selected in the alarm/event occurrence history, a display region 51 for all contents of the comment, and the "Like" button 52 for the comment (or the document). When the user, who has browsed the comment (or the document), finds the comment helpful, it is recommended that the user clicks the "Like" button 52.

Next, in step S3 in FIG. 4, when the comment or the document URL is input on the screen 40c illustrated in FIG. 9, the comment or the document is registered for the alarm/event that has occurred this time. In this case, a node of new comment and a node of document information, which are associated with the node N14a of alarm/event that has occurred this time illustrated in FIG. 10, are generated, and further, edges as indicated by the arrow S203 and the arrow S204 are set between the node of comment and the node of document information (nodes in this case are new nodes, which are not the node N15 and the node N16).

Update of Weighting Based on Behavior History of User, Reflection in Display Order The web server 12 (the presentation unit 121) can be configured to acquire the following logs as a behavior history of the user with respect to the comment or the document.

(1) most recent browsing date and time, (2) number of times of browsing/downloading, (3) browsing time (converted per page), (4) the number of times "Like" is received by users as feedback when the users felt "helpful".

Based on these, the web server 12 (the presentation unit 121) can update the weighting of each comment/document. Further, the web server 12 (the presentation unit 121) can reflect the weighting on each item on the screen, such as "A document that has been referred to in the past", and display the weights in descending order. A location where the weighting is updated in the first aid database 125 is indicated by a thick arrow in FIG. 11.

In this case, for example, the presentation unit 121 can update the weighting of each comment or the document information (the registration information) based on the behavior history of the user for the comment or the document information (the registration information), which is information that represents at least one of the most recent browsing date and time, the number of times of browsing, browsing time, and the number of times that helpful feedback is received, and for example, can present each comment or the document information (the registration information) in descending order of the weighting when there are a plurality of comments or a plurality of pieces of document information (the registration information) to be presented.

(Update of Weighting based on Attribute Information of User and Document, Reflection in Display Order) Also, the web server 12 (the presentation unit 121) may update the above-described weighting according to the attributes (years of experience, department to which the user belongs, or the like) of the user who browsed (or registered) the first aid or the document information, or the like. According to this, each item on the screen, such as a "document that has been referred to in the past", is displayed in descending order of the weighting.

Further, the weighting of the document may be updated according to the creation date and time of the document that is registered with respect to the alarm/event based on the concept that "relatively new documents have higher quality of information than documents that have old creation date and time". According to this, each item on the screen, such as a "document that has been referred to in the past", is displayed in descending order of the weighting.

In this case, for example, the presentation unit 121 can update the weighting of each comment or the document information (the registration information) based on at least one of the creation date and time of the document information (the registration information) or the attribute of the user who browsed or registered the comment or the document information (the registration information), and for example, can present each comment or the document information (the registration information) in descending order of the weighting when there are a plurality of comments or a plurality of pieces of document information (the registration information) to be presented.

Action/Effects

According to the first embodiment, it can be expected that the knowledge database will automatically grow by using the system, so that more accurate and necessary information can be quickly provided. That is, according to the first embodiment, a first aid can be appropriately presented.

Second Embodiment

Figure 12:
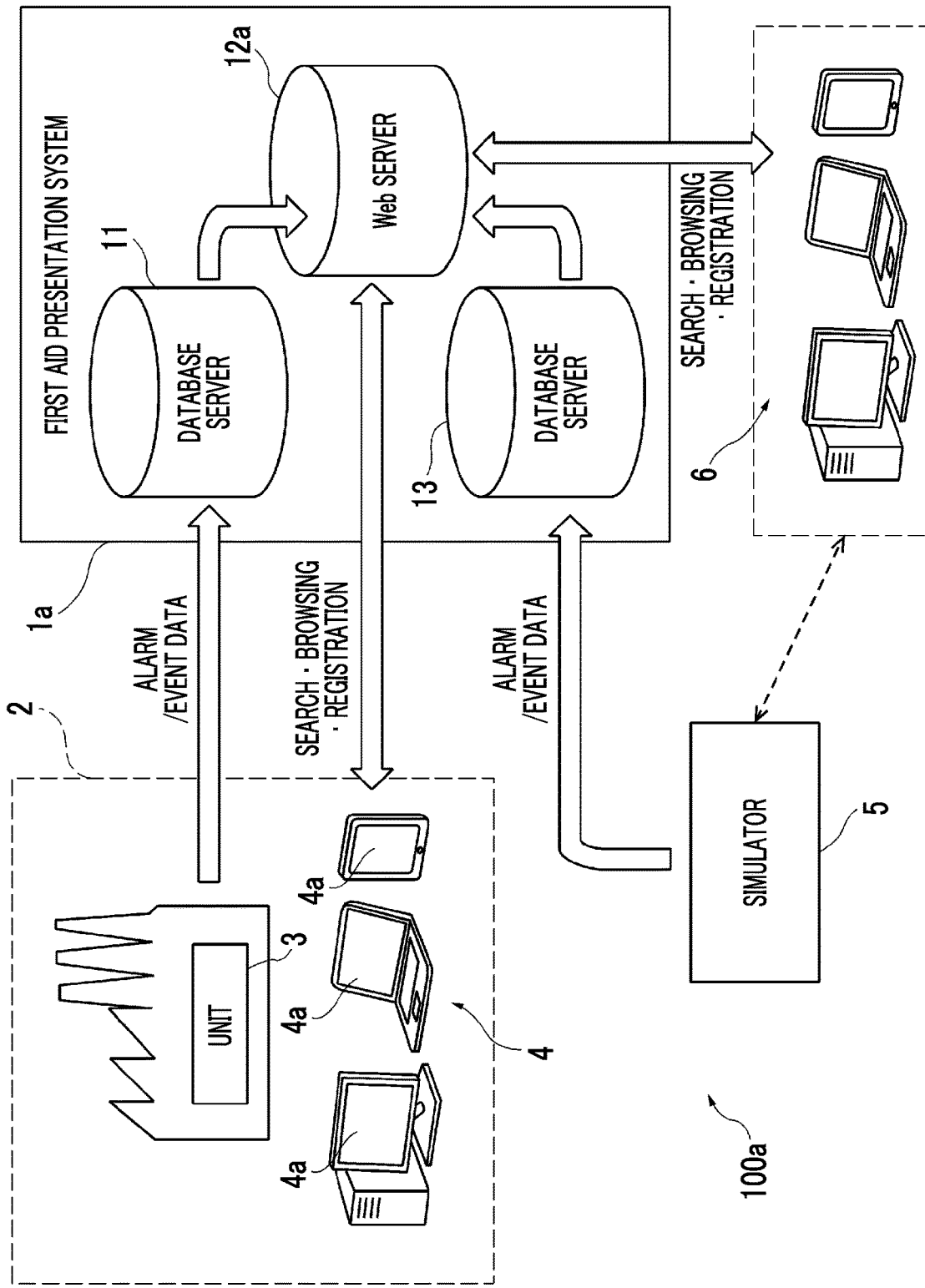
FIG. 12 is a system diagram of the first aid presentation system according to an embodiment of the present disclosure.

FIG. 12 is a system diagram of a first aid presentation system according to a second embodiment of the present disclosure. The first aid presentation system 1a illustrated in FIG. 12 is difference from the first aid presentation system 1 according to the first embodiment illustrated in FIG. 1, which uses the alarm/event data generated in the plant 2 as the monitoring target, in that the alarm/event data, which is generated by a simulator 5 simulating the plant 2, is used as the monitoring target. In the second embodiment, for example, by utilizing the simulator 5, it is possible to build a mechanism capable of accumulating and utilizing knowledge for an alarm (hereinafter, referred to as a "rare alarm") that occurs less frequently in actual operation. The web server 12a has basically the same configuration as the web server 12 illustrated in FIG. 2, and one first aid database 125 is shared for alarm/event data from the plant 2 and alarm/event data from the simulator 5.

The simulator 5 simulates an operation of each unit of the plant 2 and generates alarm data by, for example, using a machine learning model or using a model in which a physical model and a simple model are combined. The operation of the simulator 5 is performed, for example, from a user terminal 6. In this case, it is desirable that the simulator 5 has, for example, the following functions.

That is, the simulator 5 desirably includes a plant operation (activate/stop), execution speed change of the simulation, a backtrack function (return a simulator state to a past state and retrain), setting change of an operation condition (for example: atmospheric temperature, cooling water temperature, or the like), a setting of accident item, and a pseudo generation function.

Further, the first aid presentation system 1a can select an "actual operation mode" and a "training mode", and can be switched between an "actual plant environment" by the database server 11 and a "simulator environment" by the database server 13 according to the mode. That is, the first aid presentation system 1a newly includes the database server 13 that accumulates the alarm data generated by the simulator 5. Further, the web server 12a performs presentation of a first aid with respect to the user terminal 4 and update of the first aid database 125 based on the alarm data generated by the plant 2 in the "actual operation mode", and performs presentation of a first aid with respect to the user terminal 6 and update of the first aid database 125 based on the alarm data generated by the simulator 5 in the "training mode".

In this case, it is possible to accumulate knowledge for an alarm first aid by utilizing the training data generated by the simulator 5. When the "training mode" is selected, for example, the rare alarm that is pseudo-generated on a simulator side is displayed in a list on the "alarm/event feed" screen 40a illustrated in FIG. 5. For example, when it is desired to perform operation training related to the alarm first aid, a trainee selects each rare alarm on the feed screen 40a. Accordingly, by checking the first aid for each alarm (hereinafter, referred to as the first aid) and the recommended document, training of an alarm first aid can be performed.

By registering the comment as knowledge, a cause/first aid content or the like for the rare alarm that is trained during training can be referenced when the same alarm occurs in actual operation. Note that, the document/comment information that is obtained in each mode may be identified, and in particular, the document/comment information that is obtained in the "actual operation mode" may be given a higher weight and displayed higher on the screen.

Action/Effects

According to the second embodiment, it is possible to improve the accuracy of knowledge by aggregating knowledge for the pseudo-generated rare alarm in one knowledge base, in addition to knowledge for the alarm that occur in actual operation. Further, since an operator can check, register, and update the knowledge for various alarms including the rare alarm, it can be expected that the operator's ability to deal with troubles will be improved.

Other Embodiments

The embodiments of the present disclosure have been described in detail with reference to the drawings. However, the specific configuration is not limited to the embodiments of the present disclosure, and includes design changes and the like without departing from the gist of the present disclosure.

In the above embodiment, although only one plant 2 is used as the monitoring target, the present disclosure is not limited to this, and for example, a plurality of plants 2 may be used as monitoring targets. Further, the monitoring target is not limited to the plant 2, and a device, an apparatus, or a unit that is not installed in the plant may be used as the monitoring target. Further, the first aid database 125 is not limited to the graph database, and may be a database of another format or may be a combination of a database of another format and the graph database.

Computer Configuration

Figure 13:
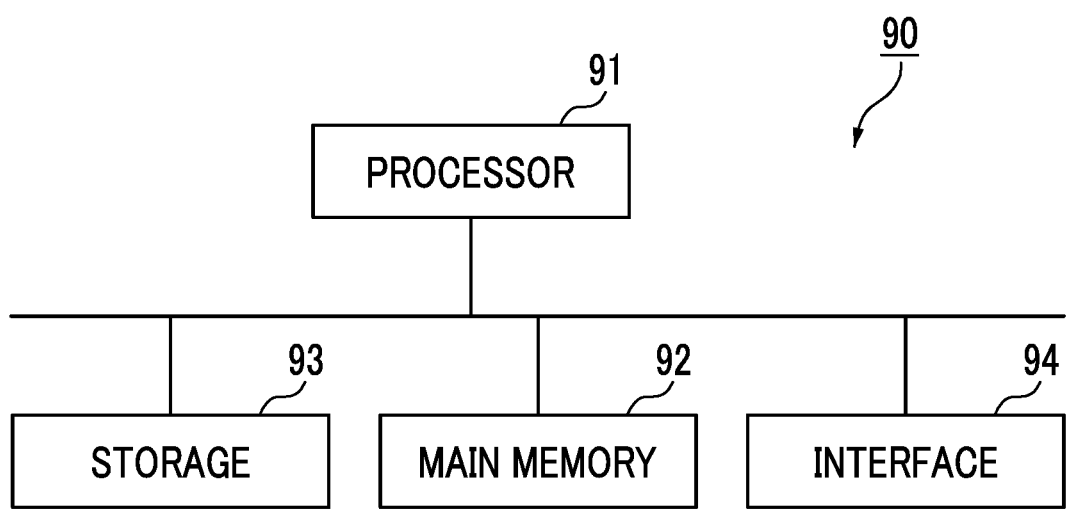
FIG. 13 is a schematic block diagram illustrating a configuration of a computer according to at least one embodiment.

FIG. 13 is a schematic block diagram showing a configuration of a computer according to at least one embodiment.

The computer 90 includes a processor 91, a main memory 92, a storage 93, and an interface 94.

The above-described first aid presentation systems 1 and 1a are implemented in the computer 90. An operation of each processing unit described above is stored in the storage 93 in the form of a program. The processor 91 reads the program from the storage 93, loads the program into the main memory 92, and executes the above process according to the program. Further, the processor 91 secures a storage area corresponding to each of the above-mentioned storage units in the main memory 92 according to the program.

The program may be a program for realizing a part of the functions exerted by the computer 90. For example, the program may exhibit its function by using a combination with other programs already stored in storage or by using a combination with other programs implemented on other devices. In another embodiment, the computer may include a custom large scale integrated circuit (LSI) such as a programmable logic device (PLD) in addition to or instead of the above configuration. Examples of the PLD include a programmable array logic (PAL), a generic array logic (GAL), a complex programmable logic device (CPLD), and a field programmable gate array (FPGA). In this case, a part or all of the functions realized by the processor may be realized by the integrated circuit.

Examples of the storage 93 include a hard disk drive (HDD), a solid state drive (SSD), a magnetic disk, a magneto-optical disk, a compact disc read only memory (CD-ROM), a digital versatile disc read only memory (DVD-ROM), and a semiconductor memory. The storage 93 may be an internal medium directly connected to a bus in the computer or may be an external medium connected to the computer via an interface 94 or via a communication line. Further, when this program is distributed to the computer 90 by using the communication line, the computer 90, in which the program is distributed, may load the program in the main memory 92 and execute the above process. In at least one embodiment, the storage 93 is a non-temporary tangible storage medium.

Additional Notes

The first aid presentation systems 1 and 1a described in each embodiment are grasped as follows, for example.

(1) A first aid presentation system (1, 1a) according to a first aspect includes:
- a storage unit 124 that stores one or a plurality of pieces of notification information (node N14b) associated with notification information (alarm/event data, node N14a) received from one or a plurality of monitoring targets (plant 2, unit 3), information (node N13) representing a first aid for the monitoring target with respect to the notification information, and one or a plurality of pieces of registration information (nodes N15, N16) registered by a user;
- a presentation unit 121 that acquires, from the storage unit, the first aid with respect to notification information (node N14b) associated with designated notification information (node N14a) and the one or the plurality of pieces of registration information, and that presents the first aid and the one or the plurality of pieces of registration information; and
- a registration unit 122 that newly registers the registration information with respect to the designated notification information. According to the present aspect and each of the following aspects, the first aid can be appropriately presented.

(2) In the first aid presentation system (1, 1a) of a second aspect according to the first aid presentation system (1, 1a) of (1), the registration information is information that represents at least one of a comment (node N15), which is related to the first aid for the monitoring target related to the designated notification information, or a document (node N16), which is referenced at the time of the first aid for the monitoring target related to the designated notification information.

(3) In the first aid presentation system (1, 1a) of a third aspect according to the first aid presentation system (1, 1a) of (1) or (2), the presentation unit 121 updates a weighting of each of pieces of the registration information based on a behavior history of the user with respect to the registration information, which represents at least one of a most recent browsing date and time, the number of times of browsing, browsing time, and the number of times that helpful feedback is received, and presents each of pieces of the registration information in descending order of weight when a plurality of pieces of the registration information to be presented are present.

(4) In the first aid presentation system (1, 1a) of a fourth aspect according to the first aid presentation system (1, 1a) of any one of (1) to (3),
the presentation unit 121 updates a weighting of each of pieces of the registration information based on at least one of creation date and time of the registration information or an attribute of the user who browsed or registered the registration information, and presents each of pieces of the registration information in descending order of weight when a plurality of pieces of the registration information to be presented are present.

(5) In the first aid presentation system (1a) of a fifth aspect according to the first aid presentation system (1a) of any one of (1) to (4), the storage unit 124 further stores one or a plurality of pieces of notification information associated with notification information received from a simulator 5 and one or a plurality of pieces of the registration information registered by the user with respect to the notification information.

(6) In the first aid presentation system (1, 1a) of a sixth aspect according to the first aid presentation system (1a) of any one of (1) to (5), the notification information is information that includes at least one of information related to an event generated from the monitoring target or information related to an alarm.

INDUSTRIAL APPLICABILITY

According to each aspect of the present invention, a first aid can be appropriately presented.

REFERENCE SIGNS LIST 1, 1a: first aid presentation system
2: plant
3: unit
4, 6: user terminal
11, 13: database server
12: web server
121: presentation unit
122: registration unit
123: database management unit
124: storage unit
125: first aid database

The invention claimed is:
1. A first aid presentation system comprising:
a storage unit that stores a plurality of pieces of notification information which are the same or similar with notification information received from one or a plurality of monitoring targets and thereby associated with the notification information received from the one or the plurality of monitoring targets, information representing a first aid for the monitoring target with respect to each of the plurality of pieces of notification information, and one or a plurality of pieces of registration information registered by a user with respect to each of the plurality of pieces of notification information;
a presentation unit that acquires, from the storage unit, information indicating the first aid with respect to the plurality of pieces of notification information associated with designated notification information designated by the user and the one or the plurality of pieces of registration information, and that presents the first aid and the one or the plurality of pieces of registration information; and a registration unit that newly registers the registration information with respect to the designated notification information designated by the user, wherein the registration information includes information that represents a document which is referenced at the time of the first aid for the monitoring target related to the designated notification information, wherein the storage unit includes a first aid database, wherein the first aid database includes a graph database which is represented by a node which represents a target object of information, an edge which represents a relationship between the nodes, and a property which represents attributes of the node and the edge, wherein the graph database includes:
- a notification information node which represents the notification information;
- a notification information master node which represents a master information of the notification information;
- a document information node which represents information which represents the document;
- an edge which represents a relationship between the notification information node and the notification information master node; and
- an edge which represents a relationship between the notification information node and the document information node;

wherein the presentation unit, from the graph database:
- acquires a notification information master information corresponding to the notification information designated by the user;
- acquires a plurality of pieces of notification information associated with the notification information master information which is acquired; and
- acquires and presents information which represents the document which is associated with respect to each of the plurality of pieces of notification information.

2. The first aid presentation system according to claim 1, wherein
the registration information includes information that represents a comment, which is related to the first aid for the monitoring target related to the designated notification information designated by the user.

3. The first aid presentation system according to claim 1, wherein
the presentation unit updates a weighting of each of pieces of the registration information based on a behavior history of the user with respect to the registration information, which represents at least one of a most recent browsing date and time, the number of times of browsing, browsing time, and the number of times that helpful feedback is received, and presents each of pieces of the registration information in descending order of weight when a plurality of pieces of the registration information to be presented are present.

4. The first aid presentation system according to claim 1, wherein
the presentation unit updates a weighting of each of pieces of the registration information based on at least one of creation date and time of the registration information or an attribute of the user who browsed or registered the registration information, and presents each of pieces of the registration information in descending order of weight when a plurality of pieces of the registration information to be presented are present.

5. The first aid presentation system according to claim 1, wherein
the storage unit further stores one or a plurality of pieces of notification information associated with notification information received from a simulator and one or a plurality of pieces of the registration information registered by the user with respect to the notification information.

6. The first aid presentation system according to claim 1, wherein
the notification information is information that includes at least one of information related to an event generated from the monitoring target or information related to an alarm.

7. A first aid presentation method comprising:
by using a storage unit that stores a plurality of pieces of notification information which are the same or similar with notification information received from one or a plurality of monitoring targets and thereby associated with the notification information received from the one or the plurality of monitoring targets, information representing a first aid for the monitoring target with respect to each of the plurality of pieces of notification information, and one or a plurality of pieces of registration information registered by a user with respect to each of the plurality of pieces of notification information;

a presentation step of acquiring, from the storage unit, information indicating the first aid with respect to the plurality of pieces of notification information associated with designated notification information designated by the user and the one or the plurality of pieces of registration information, and presenting the first aid and the one or the plurality of pieces of registration information; and a registration step of newly registering the registration information with respect to the designated notification information designated by the user, wherein the registration information includes information that represents a document which is referenced at the time of the first aid for the monitoring target related to the designated notification information, wherein the storage unit includes a first aid database, wherein the first aid database includes a graph database which is represented by a node which represents a target object of information, an edge which represents a relationship between the nodes, and a property which represents attributes of the node and the edge, wherein the graph database includes:
- a notification information node which represents the notification information;
- a notification information master node which represents a master information of the notification information;
- a document information node which represents information which represents the document;
- an edge which represents a relationship between the notification information node and the notification information master node; and
- an edge which represents a relationship between the notification information node and the document information node;

wherein, in the presentation step, from the graph database:
- acquiring a notification information master information corresponding to the notification information designated by the user;
- acquiring a plurality of pieces of notification information associated with the notification information master information which is acquired; and acquiring and presenting information which represents the document which is associated with respect to each of the plurality of pieces of notification information.

8. A non-transitory computer-readable recording medium storing a program for causing a computer to execute:
by using a storage unit that stores a plurality of pieces of notification information which are the same or similar with notification information received from one or a plurality of monitoring targets and thereby associated with the notification information received from the one or the plurality of monitoring targets, information representing a first aid for the monitoring target with respect to each of the plurality of pieces of notification information, and one or a plurality of pieces of registration information registered by a user with respect to each of the plurality of pieces of notification information;
a presentation step of acquiring, from the storage unit, information indicating the first aid with respect to the plurality of pieces of notification information associated with designated notification information designated by the user and the one or the plurality of pieces of registration information, and presenting the first aid and the one or the plurality of pieces of registration information; and
a registration step of newly registering the registration information with respect to the designated notification information designated by the user,
wherein the registration information includes information that represents a document which is referenced at the time of the first aid for the monitoring target related to the designated notification information,
wherein the storage unit includes a first aid database,
wherein the first aid database includes a graph database which is represented by a node which represents a target object of information, an edge which represents a relationship between the nodes, and a property which represents attributes of the node and the edge,
wherein the graph database includes:
  a notification information node which represents the notification information;
  a notification information master node which represents a master information of the notification information;
  a document information node which represents information which represents the document;
  an edge which represents a relationship between the notification information node and the notification information master node; and
  an edge which represents a relationship between the notification information node and the document information node;
wherein, in the presentation step, from the graph database:
  acquiring a notification information master information corresponding to the notification information designated by the user;
  acquiring a plurality of pieces of notification information associated with the notification information master information which is acquired; and
  acquiring and presenting information which represents the document which is associated with respect to each of the plurality of pieces of notification information.

\* \* \* \* \*